US005088926A

United States Patent [19]
Lang

[11] Patent Number: 5,088,926
[45] Date of Patent: Feb. 18, 1992

[54] IMPLANT FOR THE JAWBONE

[76] Inventor: Manfred Lang, Kaiserstrasse 18-20, 8500 Nuremberg 1, Fed. Rep. of Germany

[21] Appl. No.: 627,719

[22] Filed: Dec. 14, 1990

[30] Foreign Application Priority Data

Jan. 5, 1990 [DE] Fed. Rep. of Germany ....... 9000076

[51] Int. Cl.⁵ .................. A61C 8/00; A61C 5/08
[52] U.S. Cl. .................... 433/173; 433/221; 433/174
[58] Field of Search ............... 433/173, 174, 175, 221

[56] References Cited

U.S. PATENT DOCUMENTS

| | | | |
|---|---|---|---|
| 4,406,623 | 9/1983 | Gratelmann et al. | 433/174 |
| 4,480,997 | 11/1984 | Deutsch et al. | 433/221 |
| 4,626,214 | 12/1986 | Artal | 433/174 |
| 4,744,754 | 5/1988 | Ross | 433/173 |
| 4,780,081 | 10/1988 | Enomoto et al. | 433/174 |
| 4,904,187 | 2/1990 | Zingheim | 433/173 |
| 4,932,870 | 6/1990 | Miller | 433/221 |

Primary Examiner—Robert P. Swiatek
Assistant Examiner—Nicholas D. Lucchesi
Attorney, Agent, or Firm—Toren, McGeady & Associates

[57] ABSTRACT

An implant for the jawbone includes a shaft portion and a conical retention portion which is provided with displacement projections. The displacement projections are sickle-shaped retention wedges which are provided on the retention portion located opposite each other. Since the retention portion is conical and the retention wedges result in an oval cross-section, the implant can be inserted into the prepared alveolus having the same shape and a rotation of at most 90° results in locking of the implant in the interradicular alveolar bone to provide primary stability.

3 Claims, 1 Drawing Sheet

IMPLANT FOR THE JAWBONE

BACKGROUND OF THE INVENTION

1. Field of the Invention

The present invention relates to an implant for the human jawbone with a shaft portion and a conical retention portion which is provided with displacement projections.

2. Description of the Related Art

An implant known from German patent 31 36 602 includes a self-tapping or self-cutting screw with a continuous helical thread. For implanting the known implant, a hole is drilled in the jawbone by means of the core diameter of the shaft portion. The implant cuts the thread entirely by itself. This implant requires a boring depth which extends beyond the bottom of the alveolus into the jawbone in order to obtain a sufficient primary stability.

SUMMARY OF THE INVENTION

It is an object of the present invention to provide an implant of the above-described type which can be inserted into the prepared alveolus and which is retained solely in the alveolar bone and does not require a borehole extending into the jawbone.

In accordance with the present invention, the displacement projections of the conical retention portion of the implant are sickle-shaped retention wedges which are located on the retention portion diametrically opposite each other.

Other implants, such as, screws or cylinders with greater diameters or the so-called "Tubingen Instant Implant", cannot penetrate into the interradicular alveolus bone as deeply as the single-tooth implant according to the present invention. This is significant for a good primary stability.

The anatomical shape of a root of a tooth and of the alveolus receiving the root is conical and oval in cross-section, wherein the wide sides of the roots of the teeth are located next to each other. In the X-ray image, this results in a pyramid-shaped bone structure between the individual roots of the teeth, i.e., interradicular alveolar bone, in such a way that the tips of the pyramids are directed in direction of the tooth crowns. The shape of the implant according to this invention is based on this anatomical structure of the alveolar bone. Since the retention portion is conical and the retention wedges have an oval cross-section, the single-tooth implant according to the present invention can be inserted with the same shape into the prepared alveolus. When the implant is rotated by at most 90°, the retention wedges penetrate into the pyramid-shaped alveolar bone. This results in a locking or wedging of the implant in the interradicular alveolar bone.

The implant according to the present invention is a so-called two-phase implant which is implanted into the respective alveolus immediately after the tooth has been removed. After a short healing period, the implant is exposed at the post penetration location, the implant post is screwed in and a ceramic dental crown is mounted. Thus, it is no longer necessary as in the past to prepare a complicated and expensive bridge construction which also required grinding of the adjacent teeth. Moreover, the implant according to the present invention prevents the usually occurring bone loss, i.e., atrophy due to inactivity, in the toothless jaw portion. This is of particular aesthetic significance especially in the front portion of the upper jaw.

In accordance with a particularly useful and advantageous feature of the invention, the retention wedges are slightly inclined in circumferential direction. The inclination of the retention wedges causes the implant during locking to be forced slightly downwardly into the alveolus which further improves the necessary primary stability and may also result in a quick stop of bleeding. This, in turn, facilitates the filling of the free spaces with absorbable bone replacement material. In addition, the criteria of the so-called pressure osteosynthesis known from orthopedics are fully taken into consideration.

The shaft portion is usually cylindrical in cross-section and determines the total length of the single-tooth implant. The rotation for locking the implant usually takes place in a clockwise direction. The retention wedges are provided in pairs offset relative to each other by 180°.

In accordance with another particularly useful and advantageous feature, the retention portion has a free end which is rounded and provided with notches or indentations. When the implant is inserted, these retention notches result in a certain material distribution in the bottom of the alveolus.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

DESCRIPTION OF THE PREFERRED EMBODIMENT

Figure 1:
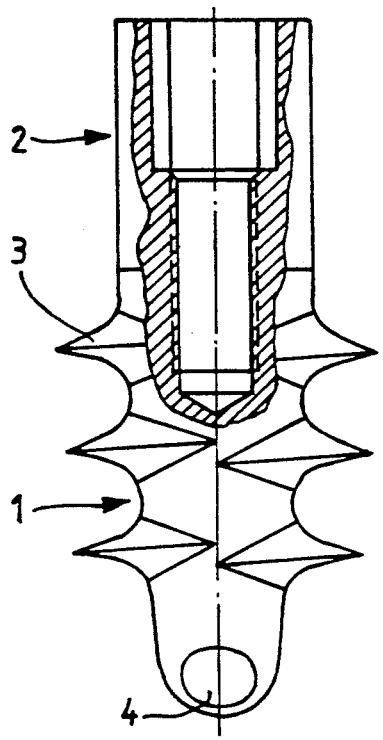
FIG. 1 is a side view, partially in section, of an implant according to the present invention.

The drawing shows the implant according to the present invention. The implant essentially consists of titanium or a titanium alloy.

Figure 2:
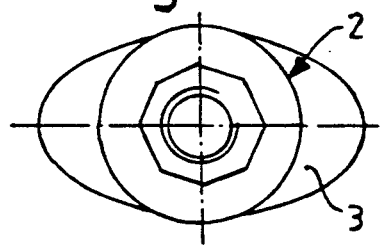
FIG. 2 is a top view of the implant of FIG. 1.
Figure 4:
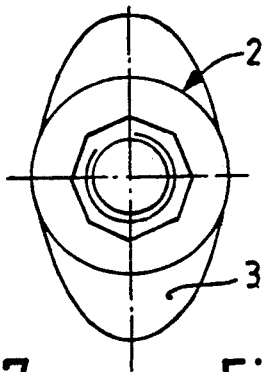
FIG. 4 is a top view of the implant of FIG. 3.
Figure 5:
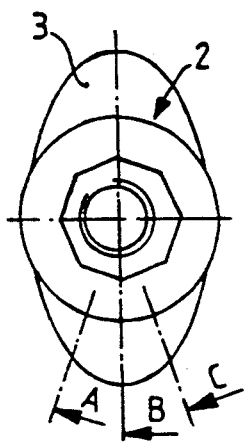
FIG. 5 is a top view of the implant of FIG. 1 showing sectional lines.

The implant includes a lower conical retention portion 1 and an upper cylindrical shaft portion 2. Sickle-shaped retention wedges 3 are provided on the retention portion 1 in such a way that they impart an oval shape to the implant in the top view of FIG. 2. The term "sickle-shaped" describes the shape of the retention wedges 3 in circumferential direction along the retention portion 1. Specifically, the shape of the retention wedges 3 is such that the radial dimension of the outer edge of each wedge from the inner circumference of the retention portion increases in circumferential direction from zero to a maximum value and then decreases to zero.

The retention wedges 3 are slightly inclined relative to a plane extending perpendicularly to the center axis. The lower end of the implant is rounded and provided with retention notches 4.

An implant post, not shown, and a closing cap, also not shown, are part of the implant and are replaceable.

Figure 3:
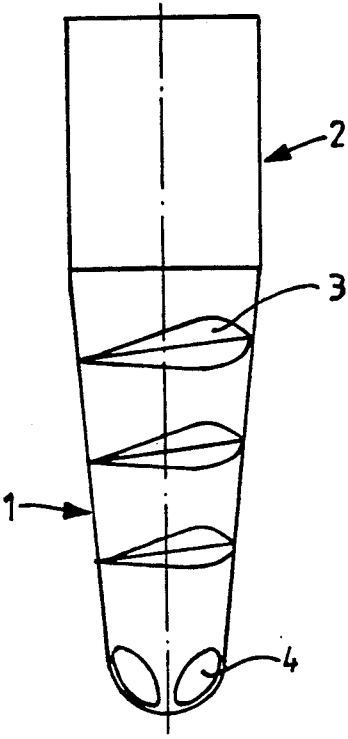
FIG. 3 is a side view of the implant of FIG. 1, turned by 90°.
Figure 6:
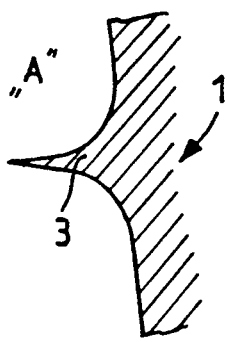
FIG. 6 is a sectional view, on a larger scale, along sectional line A of FIG. 5.
Figure 7:
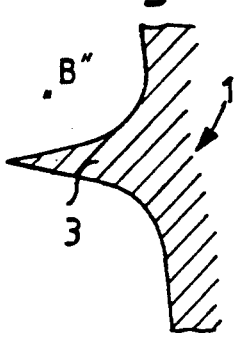
FIG. 7 is a sectional view, on a larger scale, along sectional line B of FIG. 5.
Figure 8:
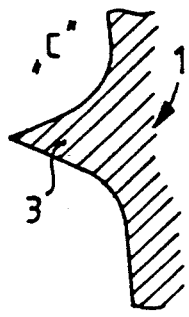
FIG. 8 is a sectional view, on a larger scale, along sectional line C of FIG. 5.

Each sickle-shaped retention wedge 3 whose width narrows radially outwardly has a conical shape as shown in FIG. 3 and as described as follows: The axial thickness of the retention wedge 3 increases in circumferential direction to a maximum thickness and then conically decreases. This is also clear from the sectional views of FIGS. 6 to 8. Each retention wedge 3 extends at the base thereof 180 around the retention portion 1 which is of round cross-section.

While a specific embodiment of the invention has been shown and described in detail to illustrate the application of the inventive principle, it will be understood that the invention may be embodied otherwise without departing from such principles.

I claim:

1. An implant for the human jawbone, the implant including a shaft portion and a conical retention portion, the retention portion having a plurality of displacement projections, the improvement comprising the displacement projections being individual wedge members, the wedge members being located in pairs on the retention portion opposite each other, wherein each wedge member is sickle-shaped such that the radial dimension of an outer edge of the wedge member from the circumference of the retention portion increases in circumferential direction from zero to a maximum value and then decreases to zero, whereby each pair of wedge members has together with the retention portion an oval shape in transverse cross-section, and wherein each wedge member is conically-shaped in radial direction with increasing width from the outer edge of the wedge member to the circumference of the retention portion, and each wedge member is conically-shaped in circumferential direction with increasing width from one end thereof at the retention portion to another end thereof at the retention portion.

2. The implant according to claim 1, wherein the retention wedges are slightly inclined in circumferential direction of the retention portion.

3. The implant according to claim 1, wherein the retention portion has a free end, the free-end of the retention portion being rounded and being provided with notches.

* * * * *